(12) United States Patent
Wang

(10) Patent No.: US 11,648,816 B2
(45) Date of Patent: May 16, 2023

(54) VEHICLE AIR-CONDITIONER TEMPERATURE CONTROLLING METHOD, VEHICLE AIR-CONDITIONER TEMPERATURE CONTROLLING SYSTEM AND STORAGE MEDIUM

(71) Applicant: BOE TECHNOLOGY GROUP CO., LTD., Beijing (CN)

(72) Inventor: Kaifeng Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 455 days.

(21) Appl. No.: 16/753,199

(22) PCT Filed: Apr. 9, 2019

(86) PCT No.: PCT/CN2019/081938
§ 371 (c)(1),
(2) Date: Apr. 2, 2020

(87) PCT Pub. No.: WO2019/218804
PCT Pub. Date: Nov. 21, 2019

(65) Prior Publication Data
US 2020/0331319 A1    Oct. 22, 2020

(30) Foreign Application Priority Data

May 16, 2018 (CN) .......................... 201810467864.2

(51) Int. Cl.
*B60H 1/00* (2006.01)

(52) U.S. Cl.
CPC ..... *B60H 1/00742* (2013.01); *B60H 1/00828* (2013.01); *B60H 1/00878* (2013.01)

(58) Field of Classification Search
CPC ............ B60H 1/00742; B60H 1/00807; B60H 1/00828
See application file for complete search history.

(56) References Cited

U.S. PATENT DOCUMENTS

2016/0262625 A1* 9/2016 Lawrenson .......... A61B 5/0077
2018/0038606 A1   2/2018 Chakravarty et al.

FOREIGN PATENT DOCUMENTS

| CN | 1492297 A | 4/2004 |
|---|---|---|
| CN | 104122864 A | 10/2014 |
| CN | 105674504 A | 6/2016 |
| CN | 106403203 A | 2/2017 |
| CN | 108891223 A | 11/2018 |
| JP | 2013012029 A | * 1/2013 |

OTHER PUBLICATIONS

The Second Chinese Office Action dated Sep. 8, 2020; Appln. No. 201810467864.2.

* cited by examiner

*Primary Examiner* — Eric S Ruppert

(57) ABSTRACT

A vehicle air-conditioner temperature controlling method, a vehicle air-conditioner temperature controlling system and a storage medium. The vehicle air-conditioner temperature controlling method includes: controlling an air-conditioner to perform heating and cooling according to a current contraction-dilation state of a vein vessel of a user.

19 Claims, 1 Drawing Sheet

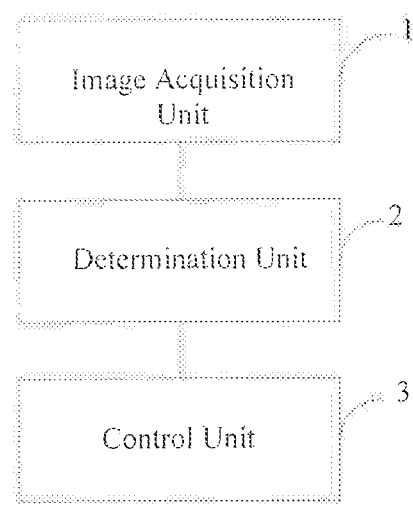

VEHICLE AIR-CONDITIONER TEMPERATURE CONTROLLING METHOD, VEHICLE AIR-CONDITIONER TEMPERATURE CONTROLLING SYSTEM AND STORAGE MEDIUM

The application claims priority of the Chinese patent application No. 201810467864.2, filed on May 16, 2018, the entire disclosure of which is incorporated herein by reference as part of the present application.

TECHNICAL FIELD

Embodiments of the present disclosure relate to a vehicle air-conditioner temperature controlling method, a vehicle air-conditioner temperature controlling system, and a storage medium.

BACKGROUND

Vehicle air-conditioner is an air-conditioner installed inside a vehicle, and controls a temperature inside the vehicle by heating and cooling, thereby providing a comfortable environment for a driver and a passenger. Generally, the vehicle air-conditioner includes components such as a compressor, a condenser, a throttling element, an evaporator, fans, and a control component.

SUMMARY

At least one embodiment of the present disclosure provides a vehicle air-conditioner temperature controlling method, including: controlling an air-conditioner to perform heating and cooling according to a current contraction-dilation state of a vein vessel of a user.

For example, in the vehicle air-conditioner temperature controlling method according to an embodiment of the present disclosure, before controlling the air-conditioner to perform heating and cooling according to the contraction-dilation state of the vein vessel of the user, the vehicle air-conditioner temperature controlling method further including: acquiring a current image of the vein vessel of the user; and comparing widths of the vein vessel at a same position in the current image and in a reference image such that, if the width of the vein blood vessel in the current image is greater than the width of the vein vessel in the reference image, the vein vessel is currently in a dilation state, otherwise the vein vessel is currently in a contraction state; the reference image is an image of the vein vessel of the user under a preset temperature.

For example, in the vehicle air-conditioner temperature controlling method according to an embodiment of the present disclosure, after controlling the air-conditioner to perform heating and cooling according to the current contraction-dilation state of the vein vessel of the user, the vehicle air-conditioner temperature controlling method further including: determining whether a command to stop acquiring the current image of the vein vessel is received; if the command is not received, acquiring the current image of the vein vessel of the user again after a preset time interval, and determining the contraction-dilation state of the vein vessel in the again acquired current image, to continue to control the air-conditioner to perform heating and cooling according to the again determined contraction-dilation state of the vein vessel; and if the command is received, stopping acquiring the current image of the vein vessel again.

For example, in the vehicle air-conditioner temperature controlling method according to an embodiment of the present disclosure, a duration of the preset time interval is in a range from 1 minute to 5 minutes.

For example, in the vehicle air-conditioner temperature controlling method according to an embodiment of the present disclosure, acquiring the current image of the vein vessel of the user includes: emitting infrared light to the vein vessel of the user; receiving reflected infrared light reflected by the vein vessel of the user from the emitted infrared light; and generating the current image from the reflected infrared light.

For example, in the vehicle air-conditioner temperature controlling method according to an embodiment of the present disclosure, before receiving the reflected infrared light reflected by the vein vessel of the user from the emitted infrared light, the vehicle air-conditioner temperature controlling method further includes: filtering the reflected infrared light reflected by the user from the emitted infrared light.

For example, in the vehicle air-conditioner temperature controlling method according to an embodiment of the present disclosure, the user includes at least one of a driver and a passenger.

For example, in the vehicle air-conditioner temperature controlling method according to an embodiment of the present disclosure, controlling the air-conditioner to perform heating and cooling according to the current contraction-dilation state of the vein vessel of the user includes: if the current contraction-dilation state of the vein vessel of the user is a contraction state, controlling the air-conditioner to perform heating; otherwise, controlling the air-conditioner to perform cooling.

For example, in the vehicle air-conditioner temperature controlling method according to an embodiment of the present disclosure, controlling the air-conditioner to perform heating includes: controlling an outlet wind speed and a heating temperature; both the outlet wind speed and the heating temperature are in positive correlation with a contraction amount of the vein vessel.

For example, in the vehicle air-conditioner temperature controlling method according to an embodiment of the present disclosure, controlling the air-conditioner to perform cooling includes: controlling an outlet wind speed and a cooling temperature; the outlet wind speed is in positive correlation with a dilation amount of the vein vessel, and the cooling temperature is in negative correlation with the dilation amount of the vein vessel.

At least one embodiment of the present disclosure further provides a vehicle air-conditioner temperature controlling system, including: an image acquisition unit, configured to acquire a current image of a vein vessel of a user; a determination unit, configured to compare widths of the vein vessel at a same position in a current image and in a reference image such that, if the width of the vein blood vessel in the current image is greater than the width of the vein vessel in the reference image, the vein vessel is currently in a dilation state, otherwise the vein vessel is currently in a contraction state, the reference image is an image of the vein vessel of the user under a preset temperature; and a control unit, configured to control an air-conditioner to perform heating and cooling according to a determination result of the determination Unit about the current contraction-dilation state of the vein vessel of the user.

For example, in the vehicle air-conditioner temperature controlling system according to an embodiment of the present disclosure, after the control unit controls the air-conditioner to perform beating and cooling according to the current contraction-dilation state of the vein vessel of the user, the decision unit is configured to determine whether a command to stop acquiring the current image of the vein vessel is received; if the command is not received, the image acquisition unit is configured to acquire the current image of the vein vessel of the user again after a preset time interval, the determination unit is configured to determine the deflation-contraction state of the vein vessel in the again acquired current image, and the control unit is configured to continue to control the air-conditioner to perform heating and cooling according to the again determined contraction-dilation state of the vein vessel; if the command is received, the image acquisition unit is configured to stop acquiring the current image of the vein vessel again.

For example, in the vehicle air-conditioner temperature controlling system according to an embodiment of the present disclosure, a duration of the preset time interval is in a range from 1 minute to 5 minutes.

For example, in the vehicle air-conditioner temperature controlling system according to an embodiment of the present disclosure, the image acquisition unit includes an infrared sensor, and the infrared sensor is configured to: emit infrared light to the vein vessel of the user; receive reflected infrared light reflected by the vein vessel of the user from the emitted infrared light; and generate the current image from the reflected infrared light.

For example, in the vehicle air-conditioner temperature controlling system according to an embodiment of the present disclosure, the image acquisition unit is further configured to: filter the reflected infrared light reflected by the user from the emitted infrared light.

For example, in the vehicle air-conditioner temperature controlling system according to an embodiment of the present disclosure, the user includes at least one of a driver and a passenger.

At least one embodiment of the present disclosure further provides a computer-readable storage medium including a computer program stored thereon; the computer program, when executed by a center processing unit, is configured to perform the above-described vehicle air-conditioner temperature controlling method.

BRIEF DESCRIPTION OF THE DRAWINGS

In order to clearly illustrate the technical solution of the embodiments of the disclosure, the drawings of the embodiments will be briefly described in the following. It is obvious that the described drawings are only related to some embodiments of the disclosure and thus are not limitative of the disclosure.

FIG. 1 is a schematic diagram of a vehicle air-conditioner temperature controlling system according to an embodiment of the present invention.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and claims of the present disclosure, are not intended to indicate any sequence, amount or importance, but distinguish various components. Also, the terms "comprises" or "includes," etc., are intended to specify that the elements or the objects stated before these terms encompass the elements or the objects listed after these terms as well as equivalents thereof, but do not exclude other elements or objects. The phrases "connect", "connected", etc., are not intended to define a physical connection or mechanical connection, but may include an electrical connection, directly or indirectly.

At present, with the development of technology, a vehicle-mounted manual air-conditioner has been gradually replaced by a vehicle-mounted automatic air-conditioner. The existing vehicle-mounted automatic air-conditioner generally performs heating or cooling control by collecting an ambient temperature in a vehicle compartment. When the temperature in the compartment is greater than a preset value, the cooling control is performed; and when the temperature in the compartment is less than the preset value, the heating control is performed. However, people have different feelings for temperatures. For example, a person who is more sensitive to temperature may already feel hot even the body temperature has not been greater than the preset value, but heating is still being performed at this time according to the current control logic of the vehicle air-conditioner. As a result, personalized requirements of the driver and the passenger for automatic air-conditioner control cannot be satisfied.

An embodiment of the present disclosure provides a vehicle air-conditioner temperature controlling method, which controls the air-conditioner to perform heating and cooling according to a current contraction-dilation state of a vein vessel of a user (for example, a driver).

For example, when the vehicle air-conditioner is turned on, the current contraction-dilation state of the vein vessel of the driver can be determined automatically; alternatively, when the vehicle air-conditioner is turned on, a display screen of the vehicle air-conditioner displays a prompt of whether to determine the contraction-dilation state of the vein vessel, so that the driver can decide whether to determine the vein contraction-dilation state of the vein vessel. The prompt of whether to determine the contraction-dilation state of the vein vessel herein can include not only a prompt of whether to determine the contraction-dilation state but also a prompt of whether to acquire the current state of the vein vessel. The current state of the vein vessel can be acquired by means of infrared photography.

According the above-mentioned vehicle air-conditioner temperature controlling method, the air-conditioner is controlled to perform heating and cooling according to a current deflation-contraction state of the vein vessel of the driver. Compared to the existing heating and cooling control by measuring the temperature in the vehicle compartment, the above-mentioned vehicle air-conditioner temperature controlling method achieves high-level personalization and real-time performance by considering the driver's actual physical sensation in such a manner that: when the vein vessel of the driver is in the contraction state, it means that the driver feels cold, and in this case, the heating control is performed; when the vein vessel of the driver is in the dilation state, it means that the driver feels hot, and in this case, the cooling control is performed.

For example, in the vehicle air-conditioner temperature controlling method according to the embodiment of the present disclosure, the above-mentioned user includes at least one of the driver and the passenger.

The vehicle air-conditioner temperature controlling method according to an embodiment of the present disclosure will be described below with reference to the case where the user is the driver, by way of example.

For example, before controlling the air-conditioner to perform heating or cooling according to the current contraction-dilation state of the vein vessel of the driver, the vehicle air-conditioner temperature controlling method further includes the following steps S101-S102:

Step S101: acquiring a current image of a vein vessel of a driver.

For example, a current image of a vein vessel of a driver can be acquired by an image acquisition unit in a vehicle air-conditioner temperature controlling device. For example, the above-mentioned image acquisition unit can include an infrared sensor. The infrared sensor can acquire the current image of the vein vessel of the driver by transmitting infrared light to the driver and receiving infrared light reflected by the driver. It should be noted that, the way of acquiring the current image of the vein vessel of the driver includes, but is not limited to, the infrared photography. In this case, the driver is photographed to acquire the current image of the vein vessel of the driver, and the current image shows a width of the vein vessel of driver at the time of photographing.

Step S102: comparing widths at a same position of the vein vessel in the current image and in a reference image. If the width of the vein vessel in the current image is greater than the width of the vein vessel in the reference image, the vein vessel is currently in a dilation state; otherwise, it is in a contraction state; the reference image is an image of the vein vessel of the driver under a preset temperature.

For example, when the driver feels at a comfortable temperature, for example, but not limited to 24° C., an image of the vein vessel of the driver under this temperature is acquired, and the image of the vein vessel under this temperature is used as the reference image to determine the current state of the driver who uses the air-conditioner. In determining, the widths of the vein vessel at the same position in the current image and in the reference image are compared with each other. If the width of the vein vessel in the current image is greater than the width of the vein blood vessel in the reference image, the vein vessel is currently in the dilation state; otherwise, it is in the contraction state. The dilation state indicates that the driver's current feel for the temperature is being hot, and the contraction state indicates that the driver's current feel for the temperature is being cold. For example, the current image as acquired and the reference image can be images acquired by photographing the same vein vessel in the same part of the driver.

For example, after controlling the air-conditioner to perform heating and cooling according to the current contraction-dilation state of the vein vessel of the driver, the vehicle air-conditioner temperature controlling method farther includes:

determining whether a command to stop acquiring the current image of the vein vessel is received; if the command is not received, acquiring the current image of the vein vessel of the driver again after a preset time interval, determining the contraction-dilation state of the vein vessel in the again acquired current image, continuing to control the air-conditioner to perform heating and cooling according to the again determined contraction-dilation state; if the command is received, stopping acquiring the current image of the vein vessel. For example, a determination unit (such as a CPU) in a vehicle air-conditioner temperature controlling system can determine whether the command to stop acquiring the current image of the vein vessel is received.

By determining whether the command to acquire the current image of the vein vessel is received, the vehicle air-conditioner temperature controlling method can achieve a cycle control, and can further determine how to control the air-conditioner, so as to improve a degree of real time and an accuracy of the control.

For example, when controlling the air-conditioner to perform heating and cooling, a temperature and an outlet wind speed can be controlled at the same time. When performing the cycle control, the temperature and outlet wind speed are controlled in real time according to the contraction-dilation state of the vein vessel, until the air-conditioner is turned off or the acquisition of the current image of the vein vessel is stopped. In this way, the temperature is adjusted in real time in a customer-oriented manner, and the comfort level of the driver is improved.

For instance, in some examples, a duration of the preset time interval ranges from 1 minute to 5 minutes. When the duration of the preset time interval ranges from 1 minute to 5 minutes, the temperature can be adjusted in real time in a customer-oriented manner, and the comfort level of the driver is improved. Of course, the embodiments of the present disclosure include but are not limited to this, and the duration of the preset time interval can be determined according to actual requirements.

For example, acquiring the current image of the vein vessel of the driver can include the following steps S201-S203.

Step S201: emitting infrared light to the driver.

For example, the infrared light is emitted to the driver by an infrared light source generator, such as an infrared lamp. For example, the infrared light source generator can be placed right in front of the driver.

Step S202: receiving reflected infrared light reflected by the driver from the emitted infrared light.

For example, the reflected infrared light can be received by a CCD photosensitive sensor.

Step S203: generating a current image from the reflected infrared light.

It should be noted that, in the human body, deoxyhemoglobin in tissues around the vein vessel has an absorption to the infrared light, especially to the near-infrared light in the infrared light, which is different from that of the deoxyhemoglobin in the vein vessel. Thus, the reflected infrared light that is absorbed and reflected by the human body of the driver represents different brightness at different positions, and the current image of the vein vessel is generated according to the different brightness. Therefore, the current image of the vein vessel of the driver acquired by using the infrared light can achieve better precision and accuracy.

In addition, the visible light that can be seen by human eyes includes red light, orange light, yellow light, green light, cyan light, blue light, and violet light which are ordered according to the wavelength, from long to short. Light with a wavelength shorter than the violet light is called ultraviolet light, while light with a wavelength longer than the red light is called infrared light, and the human eyes cannot see the infrared light. However, because the CCD photosensitive sensor can sense all the light, it can receive the reflected infrared light and generate the current image.

For example, the infrared light source generator and the CCD photosensitive sensor can be arranged side by side; the infrared light source generator, such as an infrared lamp, emits infrared light to the driver, and the CCD photosensitive sensor receives the reflected infrared light reflected by the driver. When the CCD photosensitive sensor is exposed, a photodiode is excited by the reflected infrared light to release electric charges, and then the CCD photosensitive sensor controls the current generated by the photodiode to be output by a current transmission circuit. The CCD photosensitive sensor collects an electric signal generated by one time of imaging process and outputs it to an amplifier. The amplified and filtered electric signal is sent to an Analog to Digital converter (A/D), and the A/D converts the electric signal (which is an analog signal at this time) into a digital signal, which has a magnitude proportional to a strength of the electric signal, that is, a voltage level of the electric signal. These values are the data of the current image. For example, the data of the current image can also be post-processed by a digital signal processor (DSP) for color correction, white balance processing (depending on the user's setting in the camera) or the like, and be encoded into data formats such as image format and resolution. In addition, the current image is acquired by emitting the infrared light to the driver without using the infrared radiation emitted by the human body itself, which can further increase a precision of the vein vessel in the current image, thereby improving an accuracy in determining the contraction-dilation state of the vein vessel.

For example, before receiving the reflected infrared light reflected by the driver from the emitted infrared light, the method further includes: filtering the reflected infrared light reflected by the driver from the emitted infrared light, thereby improving the precision and reducing an interference from external light.

For example, a light filter can be provided in front of the CCD photosensitive sensor, so that the infrared light within a certain waveband can pass through the light filter but visible light and ultraviolet light are absorbed or reflected.

For example, in order to improve the precision and reduce the interference from external light, the reflected infrared light is filtered before it is received. For example, the reflected infrared light is filtered by a light filter with a transmission wavelength in a range between 880 nm and 970 nm, without limited thereto.

For example, controlling the air-conditioner to perform heating or cooling according to the current contraction-dilation state of the vein vessel of the driver includes:

if the vein vessel of the driver is currently in the contraction state, the air-conditioner is controlled to perform heating, otherwise the air-conditioner is controlled to perform cooling.

The dilation and contraction of the skin vessel (the vein vessel) is an important form of regulating the body temperature. In general, when the human body feels cold, the vein vessel will be contracted to maintain the body temperature; and when the human body feels hot, the vein vessel will be dilated to increase an evaporative heat dissipation efficiency. Therefore, the cooling control is performed when the vein vessel is dilated, and the heating control is performed when the vein vessel is contracted, so as to adjust the temperature according to the driver's physical sensation in real time. Such adjustment is highly targeted, which improves comfort level and reduces a frequency of manual operation to the air-conditioner.

For example, controlling the air-conditioner to perform heating includes: controlling the outlet wind speed and the heating temperature, and both of the outlet wind speed and the heating temperature are in positive correlation with a contraction amount of the vein vessel. It should be noted that, the above-mentioned "positive correlation" means that the dependent variable is increased with an increase of the independent variable; that is, the larger the contraction amount, the greater the outlet wind speed and heating temperature.

The outlet wind speed and the performed heating temperature are both in positive correlation with the contraction amount of the vein vessel, which can reduce an energy consumption under the premise of satisfying the driver's physical comfort level. When the contraction amount is small, it means that the driver's physical sense of coldness is low. When the contraction amount is large, it means that the driver's physical sense of coldness is high. Thus, when the contraction amount is small, the air-conditioner is controlled with low outlet wind speed and low cooling temperature, to satisfy the requirement of the driver; and when the contraction amount is large, the air-conditioner is controlled with high outlet wind speed and high cooling temperature to quickly increase the temperature in the vehicle compartment.

For example, controlling the air-conditioner to perform cooling includes: controlling the outlet wind speed and the cooling temperature. The outlet wind speed is in positive correlation with the dilation amount of the vein vessel, and the cooling temperature is in negative correlation with the dilation amount of the vein vessel.

The outlet wind speed is in positive correlation with the dilation amount of the vein vessel, and the cooling temperature is in negative correlation with the dilation amount of the vein vessel, so as to reduce the energy consumption under the premise of satisfying the driver's physical comfort level. When the dilation amount is small, it means that the drives physical sense of hot is low. When the dilation amount is large, it means that the driver's physical sense of hot is high. Thus, when the dilation amount is small, the air-conditioner is controlled with low outlet wind speed and high cooling temperature, to satisfy the requirement of the driver; and when the dilation amount is large, the air-conditioner is controlled with high outlet wind speed and low cooling temperature to quickly decrease the temperature in the vehicle compartment.

As shown in FIG. 1, an embodiment of the present disclosure further provides a vehicle air-conditioner temperature controlling system, including: an image acquisition unit 1, configured to acquire a current image of a vein vessel of a user (for example, a driver); a determination unit 2, configured to compare widths of the vein vessel at a same position in the current image and in a reference image, if the width of the vein blood vessel in the current image is greater than the width of the vein vessel in the reference image, the vein vessel is currently in the dilation state, otherwise the vein vessel is currently in the contraction state, in which the reference image is an image of the vein vessel of the user under a preset temperature; and a control unit 3, configured to control an air-conditioner to perform heating and cooling according to a determination result of the determination unit about the current contraction-dilation state of the vein vessel of the user.

According the above-mentioned vehicle air-conditioner temperature controlling system, the air-conditioner is controlled to perform heating and cooling according to the current deflation-contraction state of the vein vessel of the driver. Compared to the existing heating and cooling control by way of measuring the temperature in the vehicle compartment, the above-mentioned vehicle air-conditioner temperature controlling system achieves high-level personalization and real-time performance by considering the driver's actual physical sensation in such a manner that: when the vein vessel of the driver is in the contraction state, it means that the driver feels cold, and in this case, the heating control is performed; when the vein vessel of the driver is in the dilation state, it means that the driver feels hot, and in this case, the cooling control is performed.

For example, in the vehicle air-conditioner temperature controlling system according to the embodiment of the present disclosure, the above-mentioned user includes at least one of the driver and the passenger.

The vehicle air-conditioner temperature controlling system according to an embodiment of the present disclosure will be described below with reference to the case where the user is the driver, by way of example.

For instance, in some examples, after the control unit controls the air-conditioner to perform heating and cooling according to the contraction-dilation state of the vein vessel of the user, the determination unit is configured to determine whether a command to stop acquiring the current image of the vein vessel is received, if the command is not received, the image acquisition unit is configured to acquire the current image of the vein vessel of the user again after a preset time interval, the determination unit determines the deflation-contraction state of the vein vessel in the again acquired current image, and the control unit is configured to continue to control the air-conditioner to perform heating and cooling according to the again determined contraction-dilation state of the vein vessel; if the command is received, the image acquisition unit is configured to stop acquiring the current image of the vein vessel. By determining whether the command to acquire the current image of the vein vessel is received, the vehicle air-conditioner temperature controlling system can achieve a cycle control and can further determine how to control the air-conditioner, so as to improve the degree of real time and the accuracy of the control.

For instance, in some examples, a duration of a preset time interval ranges from 1 minute to 5 minutes. When the duration of the preset time interval ranges from 1 minute to 5 minutes, the temperature can be adjusted in real time in a customer-oriented manner, and the comfort level of the driver is improved. Of course, the embodiments of the present disclosure include but are not limited to this, and the duration of the preset time interval can be determined according to actual requirements.

For instance, in some examples, the image acquisition unit includes an infrared sensor configured to: emit infrared light to the vein vessel of the user; receive reflected infrared light reflected by the vein vessel of the user from the emitted infrared light; and generate the current image from the reflected infrared light. Acquiring the current image of the vein vessel of the driver by using the infrared light can achieve better precision and accuracy. For details, please refer to the related description of the vehicle air-conditioner temperature controlling method described above, which will be omitted here.

For instance, in some examples, the image acquisition unit is further configured to filter the reflected infrared light reflected by the user from the emitted infrared light, thereby improving the accuracy and reducing the interference from external light.

An embodiment of the present disclosure further provides a computer-readable storage medium on which a computer program is stored. The computer program, when executed by a center processing unit, is configured to implement the above-described vehicle air-conditioner temperature controlling method.

The following statements should be noted:

(1) The accompanying drawings involve only the structure(s) in connection with the embodiment(s) of the present disclosure, and other structure(s) can be referred to common design(s).

(2) In case of no conflict, features in one embodiment or in different embodiments can be combined.

What are described above is the embodiments of the disclosure only and not limitative to the scope of the disclosure; any of those skilled in related arts can easily conceive variations and substitutions in the technical scopes disclosed by the disclosure, which should be encompassed in protection scopes of the disclosure. Therefore, the scopes of the disclosure should be defined in the appended claims.

The invention claimed is:

1. A vehicle air-conditioner temperature controlling method, comprising:
    controlling an air-conditioner to perform heating and cooling according to a current contraction-dilation state of a vein vessel of a user, wherein
    before controlling the air-conditioner to perform heating and cooling according to the contraction-dilation state of the vein vessel of the user, the vehicle air-conditioner temperature controlling method further comprising:
    acquiring a current image of the vein vessel of the user; and
    comparing widths of the vein vessel at a same position in the current image and in a reference image such that, if the width of the vein blood vessel in the current image is greater than the width of the vein vessel in the reference image, the vein vessel is currently in a dilation state, otherwise the vein vessel is currently in a contraction state, wherein
    the reference image is an image of the vein vessel of the user under a preset temperature.

2. The vehicle air-conditioner temperature controlling method according to claim 1, wherein after controlling the air-conditioner to perform heating and cooling according to the current contraction-dilation state of the vein vessel of the user, the vehicle air-conditioner temperature controlling method further comprising:
    determining whether a command to stop acquiring the current image of the vein vessel is received; if the command is not received, acquiring the current image of the vein vessel of the user again after a preset time interval, and determining the contraction-dilation state of the vein vessel in the again acquired current image, to continue to control the air-conditioner to perform heating and cooling according to the again determined contraction-dilation state of the vein vessel; and if the command is received, stopping acquiring the current image of the vein vessel again.

3. The vehicle air-conditioner temperature controlling method according to claim 1, wherein a duration of the preset time interval is in a range from 1 minute to 5 minutes.

4. The vehicle air-conditioner temperature controlling method according to claim 1, wherein acquiring the current image of the vein vessel of the user comprises:
    emitting infrared light to the vein vessel of the user;
    receiving reflected infrared light reflected by the vein vessel of the user from the emitted infrared light; and
    generating the current image from the reflected infrared light.

5. The vehicle air-conditioner temperature controlling method according to claim 4, wherein before receiving the reflected infrared light reflected by the vein vessel of the user from the emitted infrared light, the vehicle air-conditioner temperature controlling method further comprises:
filtering the reflected infrared light reflected by the user from the emitted infrared light.

6. The vehicle air-conditioner temperature controlling method according to claim 1, wherein the user comprises at least one of a driver and a passenger.

7. The vehicle air-conditioner temperature controlling method according to claim 1, wherein controlling the air-conditioner to perform heating and cooling according to the current contraction-dilation state of the vein vessel of the user comprises:
if the current contraction-dilation state of the vein vessel of the user is a contraction state, controlling the air-conditioner to perform heating;
if the current contraction-dilation state of the vein vessel of the user is a dilation state, controlling the air-conditioner to perform cooling.

8. The vehicle air-conditioner temperature controlling method according to claim 2, wherein controlling the air-conditioner to perform heating comprises: controlling an outlet wind speed and a heating temperature, and wherein
both the outlet wind speed and the heating temperature are in positive correlation with a contraction amount of the vein vessel.

9. The vehicle air-conditioner temperature controlling method according to claim 2, wherein controlling the air-conditioner to perform cooling comprises: controlling an outlet wind speed and a cooling temperature, and wherein
the outlet wind speed is in positive correlation with a dilation amount of the vein vessel, and the cooling temperature is in negative correlation with the dilation amount of the vein vessel.

10. A vehicle air-conditioner temperature controlling system, comprising:
an image sensor, configured to acquire a current image of a vein vessel of a user;
a determination unit, configured to compare widths of the vein vessel at a same position in a current image and in a reference image such that, if the width of the vein blood vessel in the current image is greater than the width of the vein vessel in the reference image, the vein vessel is currently in a dilation state, otherwise the vein vessel is currently in a contraction state; wherein the reference image is an image of the vein vessel of the user under a preset temperature; and
a control unit, configured to control an air-conditioner to perform heating and cooling according to a determination result of the determination unit about the current contraction-dilation state of the vein vessel of the user.

11. The vehicle air-conditioner temperature controlling system according to claim 10, wherein after the control unit controls the air-conditioner to perform heating and cooling according to the current contraction-dilation state of the vein vessel of the user,
the determination unit is configured to determine whether a command to stop acquiring the current image of the vein vessel is received,
if the command is not received, the image sensor is configured to acquire the current image of the vein vessel of the user again after a preset time interval, the determination unit is configured to determine the deflation-contraction state of the vein vessel in the again acquired current image, and the control unit is configured to continue to control the air-conditioner to perform heating and cooling according to the again determined contraction-dilation state of the vein vessel;
if the command is received, the image sensor is configured to stop acquiring the current image of the vein vessel again.

12. The vehicle air-conditioner temperature controlling system according to claim 11, wherein a duration of the preset time interval is in a range from 1 minute to 5 minutes.

13. The vehicle air-conditioner temperature controlling system according to claim 10, wherein the image sensor comprises an infrared sensor, and the infrared sensor is configured to:
emit infrared light to the vein vessel of the user;
receive reflected infrared light reflected by the vein vessel of the user from the emitted infrared light; and
generate the current image from the reflected infrared light.

14. The vehicle air-conditioner temperature controlling system according to claim 13, wherein the image sensor is further configured to:
filter the reflected infrared light reflected by the user from the emitted infrared light.

15. The vehicle air-conditioner temperature controlling system according to claim 10, wherein the user comprises at least one of a driver and a passenger.

16. A computer-readable storage medium comprising a computer program stored thereon, wherein the computer program, when executed by a center processing unit, is configured to perform the vehicle air-conditioner temperature controlling method according to claim 1.

17. The vehicle air-conditioner temperature controlling system according to claim 10, wherein the control unit is configured to:
control the air-conditioner to perform heating if the current contraction-dilation state of the vein vessel of the user is a contraction state, and control the air-conditioner to perform cooling if the current contraction-dilation state of the vein vessel of the user is a dilation state.

18. The vehicle air-conditioner temperature controlling system according to claim 17, wherein the control unit is configured to control an outlet wind speed and a heating temperature, and wherein
both the outlet wind speed and the heating temperature are in positive correlation with a contraction amount of the vein vessel if the current contraction-dilation state of the vein vessel of the user is the contraction state.

19. The vehicle air-conditioner temperature controlling system according to claim 17, wherein the control unit is configured to control an outlet wind speed and a heating temperature, and wherein
the outlet wind speed is in positive correlation with a dilation amount of the vein vessel, and the cooling temperature is in negative correlation with the dilation amount of the vein vessel, if the current contraction-dilation state of the vein vessel of the user is the dilation state.

* * * * *